United States Patent [19]

Soukup

[11] Patent Number: 5,472,688
[45] Date of Patent: Dec. 5, 1995

[54] PROCESS FOR PRODUCING A HAIR CONDITIONER

[76] Inventor: Yaclav Soukup, Rua Adelia, No. 140, Apt. 302, Ilha do Governador, Rio de Janeiro - RJ, Brazil

[21] Appl. No.: 195,738

[22] Filed: Feb. 14, 1994

Related U.S. Application Data

[63] Continuation of Ser. No. 67,164, May 26, 1993, abandoned, which is a continuation of Ser. No. 751,514, Aug. 29, 1991, abandoned.

[30] Foreign Application Priority Data

Oct. 1, 1990 [BR] Brazil .................... PI9004902

[51] Int. Cl.$^6$ .................... A61K 7/075
[52] U.S. Cl. .................... 424/70.1; 424/630; 424/632; 424/638
[58] Field of Search .................... 424/70, 70.1, 630, 424/632, 638

[56] References Cited

U.S. PATENT DOCUMENTS

| | | | |
|---|---|---|---|
| 3,681,492 | 8/1972 | Kotzbauer | 424/638 |
| 4,490,389 | 12/1984 | Nelson et al. | 514/474 |
| 4,786,493 | 11/1988 | Smith et al. | 424/70 |
| 4,992,266 | 2/1991 | Knoll | 424/70 |
| 5,002,761 | 3/1991 | Mueller et al. | 424/70 |
| 5,043,162 | 8/1991 | Trager | 424/70 |
| 5,051,252 | 1/1991 | Schultz et al. | 424/71 |
| 5,077,040 | 12/1991 | Bergmann et al. | 424/70 |

*Primary Examiner*—John C. Bleutge
*Assistant Examiner*—Amy Hulina
*Attorney, Agent, or Firm*—Howard L. Rose

[57] ABSTRACT

Patent of invention "process for obtaining an hair conditioner," comprising a process for obtaining an hair conditioner which imparts gloss, softness and elasticity to the hair and augments its tendency to maintain the desired shape of the hairdo; the active ingredients of the conditioner being ascorbic acid and cupric and/or cuprous salts: the conditioner in one version being presented in powder form, containing besides the active ingredients, thickening agents, being mixed with water before use and in another version presented in form of a cream, gel or paste, to be used on hair, in both cases containing, optionally, other ingredients of specific action.

6 Claims, No Drawings

PROCESS FOR PRODUCING A HAIR CONDITIONER

This is a continuation of co-pending application Ser. No. 08/067,164, filed on May 26, 1993, now abandoned, which was a continuation of application Ser. No. 07/751,514, filed Aug. 29, 1991, now abandoned.

FIELD OF INVENTION

This invention relates to a hair conditioning product and process for producing a hair conditioner capable of increasing the gloss, softness, elasticity, and the tendency to maintain the desirable shape of the hair.

BACKGROUND OF THE INVENTION

Hair conditioners improve sensibly the aspect and the physical form of the hair treated with them. There exists a great variety of formulas for conditioning the hair. The available formulas leave much to be desired in the way of cost, ease of use and ingredients which may have an objectionable odor. Further, none of them attains the efficiency of the formulas and processes described in this invention.

OBJECT OF THE PRESENT INVENTION

It is an object of the present invention to provide a hair conditioning product having a low price and a pleasant odor.

Yet another object of this invention is to provide a hair conditioning product that is easy to use.

Still another object of the present invention is to provide a hair conditioning product that enhances the natural sheen and softness of the hair and which maintains the shape of the hair over extended periods of time.

It is another object of the present invention to provide a product that can remain in contact with the hair for long periods of time without damage to the hair.

BRIEF DESCRIPTION OF THE PRESENT INVENTION

This application presents a hair conditioner and a process for producing an entirely new conditioner employing ascorbic acid and cupric and/or cuprous salts. Ascorbic acid is vitamin C, $C_6H_8O_6$, found in many fruits, especially in the citrics, and in some vegetables with green leaves. The hair conditioner, made accordingly to this process, is presented to the user packaged as powder, which besides the active ingredients (which bring about the desired effects), contains also a thickening agent. This powder is mixed with water by the user, before application. Another form of the conditioner, from this invention, is as a convenient gel, paste or cream, which is applied directly by the user who intends to shape his or her hair. The formulations of the present invention may also include, without altering the basic concepts of the present patent application: tensoactives, humectants, and their functional equivalents or similars, besides the other compounds used in the treatment of hair shaping and conditioning, like quaternary salts, certain dyes, relaxers, etc. In order to provide a perfect and complete idea of the invention, there will be presented some examples of formulations which can be realized to attain the objectives of this invention, that is to produce an efficient hair conditioner. However, the formulas stated here stand merely as illustrative examples, which cannot be considered as delimiting this invention.

DETAILED DESCRIPTION OF THE PRESENT INVENTION

The following is an example of formulation of the present invention.

EXAMPLE NO. 1

One gram of cuprous chloride, 3 g of ascorbic acid, 5 g of ammonium chloride and 15 g of soluble starch are milled. The powder is mixed with water and applied to hair, which acquires permanent gloss, softness and elasticity noticeably superior to other conditioners used by present art.

EXAMPLE NO. 2

Half a gram of phenylenediamine chlorhydrate, 2 g of hydrated cuptic chloride, 4 g of ascorbic acid, and 5 g of ammonium chloride are dissolved in 150 ml of water, 25 g of carboxymethylcellulose are added and the mixture agitated until obtaining a homogenous paste, which is applied to the hair. The gloss, softness and elasticity of the hair are superior to the results obtained with common conditioners on the market.

EXAMPLE NO. 3

Three grams of pyrogallol, 1 g of cupric oxide, 12 ml of N-hydrochloric acid, 3 g of ascorbic acid, and 5 g of ammonium chloride are dissolved in 140 ml of water. Twenty grams of pregellified starch is added and agitated until homogenous. The hair which is treated with the resulting cream, after being washed and dried in the desired shape, undulated or stretched, shows the characteristic gloss, softness and elasticity, besides maintaining permanently its shape. Independently from these results, the hair is also tinted by the dye precursor (pyrogallol) included in the formula.

EXAMPLE NO. 4

One point six grams of pentahydrated cupric sulfate, 2.2 g of ascorbic acid, 1.3 g of ammonium chloride, and 35 g of sodium lauryl ether sulfate of 30% are dissolved in 60 ml of water. The solution, thus, obtained was used as conventional shampoo to wash hair. The washed hair, besides being clean, is glossy and soft and exhibits great tendency to keep permanently the shape in which it was dried.

Once given the disclosure, many other features, modifications and improvements will become apparent to the skilled artisan. Such other modifications, features and improvements are, therefore, considered a part of this invention, the scope of which is to be determined by the following claims.

I claim:

1. The process of producing a hair conditioner consisting of the steps of mixing cuprous chloride, ascorbic acid, ammonium chloride and a soluble starch and milling the mixture to produce a powder soluble in water.

2. The process of preparing a hair conditioner according to claim 1, wherein relative to the cuprous chloride, approximately three times as much ascorbic acid, five times as much ammonium chloride and fifteen times as much soluble starch are used in the mixture.

3. The process of conditioning hair consisting of preparing a hair conditioner of ascorbic acid and at least one copper compound dissolved in water; and shampooing the hair with the hair conditioner so prepared.

4. The process of preparing and using a hair conditioner consisting of mixing a source of copper selected from the group consisting of cuprous chloride, cupric chloride, cupric oxide and pentahydrated cupric sulfate and ascorbic acid dissolved in water, and shampooing the hair with the hair conditioner.

5. The process of preparing a hair conditioner in the form of a cream, gel or paste intended to produce gloss and softness to the hair while helping to maintain a desired shape of hair consisting of mixing ascorbic acid, one or more copper compounds selected from the group consisting of cupric and/or cuprous salts, a thickening agent, and humectants, tensoactives, quaternary salts, dyes, brighteners, modeling agents and hair relaxers.

6. The process of conditioning hair consisting of preparing a hair conditioner of ascorbic acid and at least one copper compound dissolved in water, adding ammonium chloride to the hair conditioner, and shampooing the hair with the hair conditioner so prepared.

* * * * *